United States Patent [19]
Peacock et al.

[11] Patent Number: 5,629,774
[45] Date of Patent: May 13, 1997

[54] OPTICAL SENSOR

[75] Inventors: Stanley J. Peacock, Sanderstead; Henry C. Jaggers, Slough; John S. Shaw, Blackfield, all of Great Britain

[73] Assignee: British Gas Plc, London, Great Britain

[21] Appl. No.: 537,277

[22] Filed: Sep. 29, 1995

Related U.S. Application Data

[63] Continuation of Ser. No. 90,011, filed as PCT/GB92/01723 Sep. 18, 1992, Pat. No. 5,508,809.

[30] Foreign Application Priority Data

Sep. 19, 1991 [GB] United Kingdom ............... 9120000

[51] Int. Cl.⁶ ..................................................... G01N 21/55
[52] U.S. Cl. ............................................................ 356/445
[58] Field of Search ................................................ 356/445

[56] References Cited

U.S. PATENT DOCUMENTS

| 4,997,278 | 3/1991 | Finlan et al. ........................... 356/445 |
| 5,245,410 | 9/1993 | Villuendas Yuste et al. ........... 356/445 |

Primary Examiner—Richard A. Rosenberger
Attorney, Agent, or Firm—Oblon, Spivak, McClelland, Maier & Neustadt, P.C.

[57] ABSTRACT

An optical sensor assembly includes a light source, a surface plasmon-sensitive structure for reflecting light, a light detector, and a signal indicator. The light detector receives light that is reflected from the surface plasmon-sensitive structure at an angle which is sensitive to surface plasmon absorption.

34 Claims, 7 Drawing Sheets

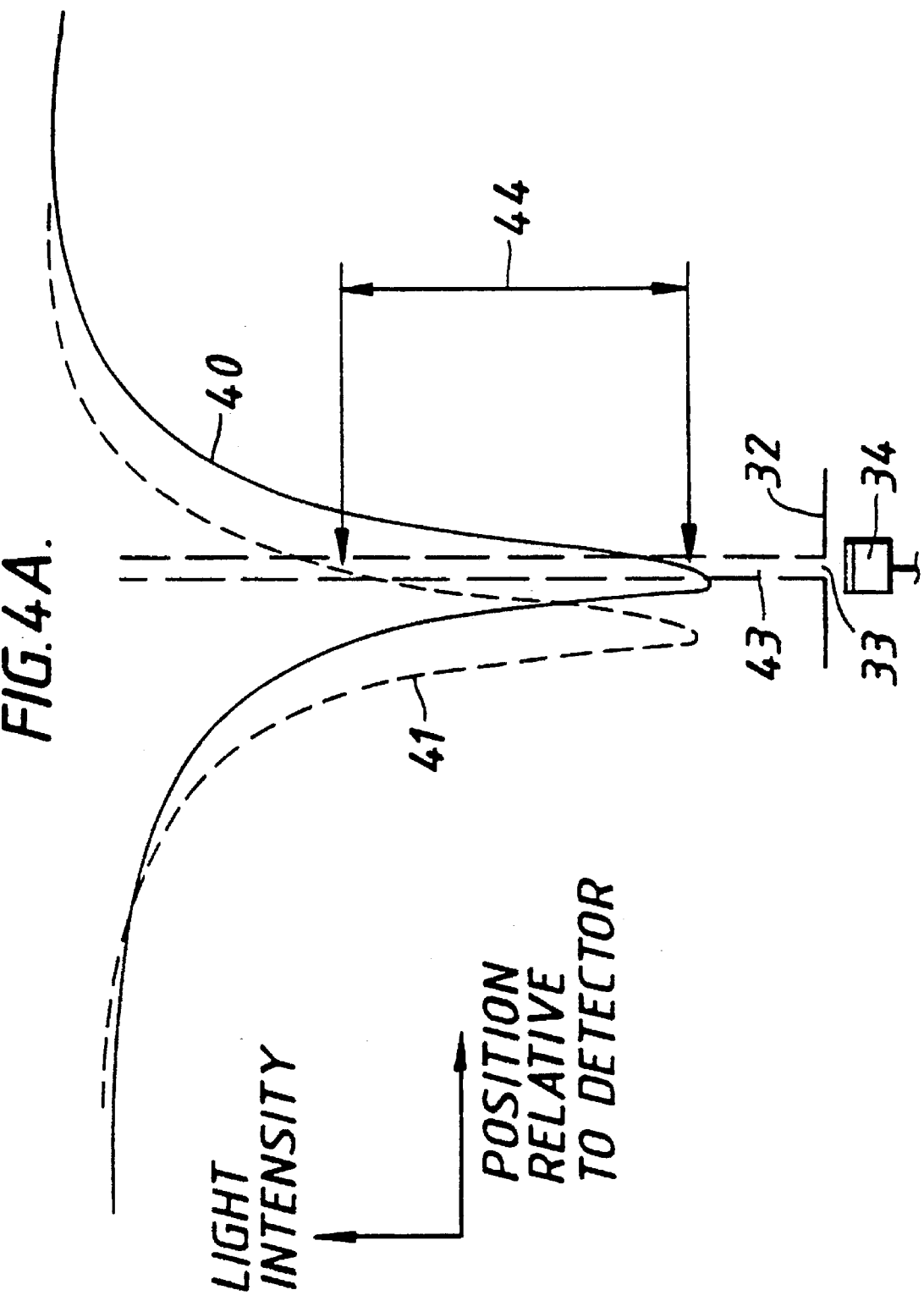

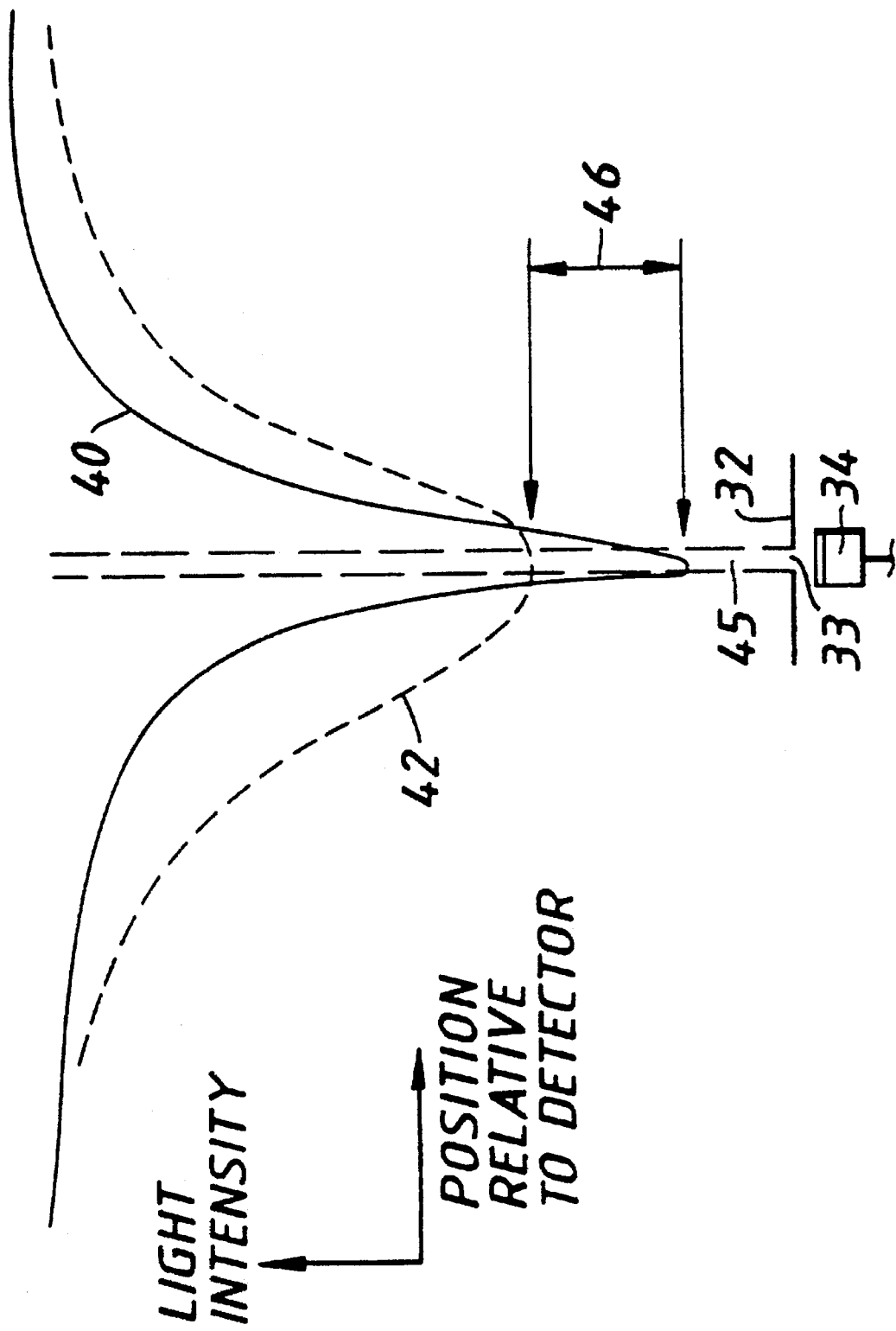

OPTICAL SENSOR

This is a Continuation of application Ser. No. 08/090,011 filed on Nov. 10, 1993, which was filed as PCT/GB92/01723 on Sep. 18, 1992, now U.S. Pat. No. 5,508,809.

BACKGROUND OF THE INVENTION

1. Field of the Invention

The present invention relates to optical sensing and, more particularly, to an optical sensor which utilises the phenomenon of surface plasmon resonance.

2. Discussion of the Background

Surface plasmons are the quanta of a surface electromagnetic wave propagating along the interface between a conducting material such as a metal and a dielectric. They represent the coupling of a longitudinal oscillation of the surface charge density with its associated electromagnetic fields. Surface plasmons can be excited by an electric field of light if the component of the wave vector of the light wave along the surface equals that of the same frequency surface wave. The effect is then called surface plasmon resonance (SPR) and may be seen as an absorption of the light. Kretschmann and Raether (Z. Naturforsch., (1968) 23a, 2135) have produced a comprehensive description of the phenomenon. The effect is strongly dependent on the dielectric properties at the metal surface and can therefore be used to sense materials at or deposited on the metal surface or to sense changes brought about in a previously existing overlayer by exposure to some other substance.

Some known forms of optical sensors utilise this phenomenon by scanning the angle of incidence or by using the so called convergent beam method. In the latter approach polarised monochromatic or narrow band light is first expanded and then focused on to a metal film coated onto the back surface of a glass prism or the front surface of a diffraction grating. The position of resonance is detected by using a linear diode array and the source of radiation or light is usually a light emitting diode which requires polarisation filters for use as an SPR source or a polarised gas laser such as a helium-neon laser.

SUMMARY OF THE INVENTION

Applicants are particularly, though not exclusively, interested in optical sensors for sensing the presence of monoethylene glycol vapour (MEG). The UK gas distribution system for distributing natural gas to premises includes many miles of pipework with lead/yarn joints. In order for such joints to remain gas tight, the packing material (jute or hemp fibres) must be maintained in a swollen state. Natural gas is a dry gas which tends to cause the packing material to dry out and shrink and possibly result in some gas leakage at the joints. To prevent this problem occurring the natural gas is conditioned with MEG which is introduced continuously in vapour form into the pipework by "fogging" units. The MEG serves as a yarn swellant. The maintenance of the correct level of MEG in the gas is important since too much results in droplets condensing on the pipe walls and in MEG being wasted, while too little results in inadequate swelling of the packing yarn thereby increasing the likelihood of some gas leakage at the joints. Thus monitoring of the concentration of the MEG in the gas at various test points throughout the system is important.

An object of the invention is to provide an optical sensor which utilises the phenomenon of surface plasmon resonance for sensing the presence of an analyte in a fluid.

According to the invention an optical sensor for sensing the presence of analyte in a fluid comprises a light source; a surface plasmon resonance-sensitive device for reflecting light originating from the light source and which device, on exposure to the analyte, responds so as to alter the intensity of the light which is reflected; a light detecting means for receiving light reflected from the device and for producing in response to the received reflected light an output signal indicative of the presence of, or representative of the concentration or a concentration range of, the analyte in the fluid; control means for controlling the portion of the reflected light which is permitted to reach the light detecting means; and indicating means for receiving a said output signal via the light detecting means and, in response thereto, indicating the presence, concentration or concentration range of the analyte in the fluid. The fluid may be gas vapour or liquid.

The control means may comprise one or more members defining or having an opening. The opening may be an aperture of fixed size defined by one member. The member may comprise a thin planar member defining a single very small hole or a 'pinhole'. Alternatively, the opening may be in the form of a slit defined by the one or more members. The control means may, alternatively, comprise an optical fibre with the bore therethrough constituting the opening. Preferably, the opening is sufficiently small to permit the passage therethrough of only a very small portion of the part of the reflected light which has been more strongly influenced by the SPR.

The light detecting means may be a photo-electric detecting means. Preferably, the photo-detecting means consists of one single photodetector, as opposed to a plurality or an array of discrete photodetectors.

The provision of a single small opening of fixed size and one single photodetector facilitates the construction of a small portable, compact unit which can be held in one hand during use.

Preferably, the light source is a diode laser. Diode lasers operating both in the visible and infrared parts of the spectrum can be used.

Since diode lasers produce polarised light a separate polarising filter does not have to be employed: thus simplifying the source optics and, again, facilitating the construction of a small unit.

The indicating means may be such as to indicate the presence of the analyte only when the signal from the light detecting means is representative of a concentration of analyte above a predetermined minimum or threshold value. Thus, the indicating means may be arranged to function in a simple on/off manner.

In another form of the sensor the indicating means may be calibrated so as to provide an indication of the concentration of the analyte in the fluid. For example, the indicating means may comprise two or more discrete indicators, each one (when activated) being representative of a different concentration or range of concentrations of the analyte in the fluid.

The two or more discrete indicators may be activated in succession as the signal from the light detecting means changes to be representative of an increased concentration of the analyte in the fluid.

The indicating means and discrete indicators may comprise one or more visual indicators such as light emitting diodes.

Alternatively, or in addition, the indicating means may produce an audible sound when activated.

The sensor may comprise a second light detecting means for receiving from the device reflected light which is unaffected by the presence of the analyte and for producing in response to the reflected light received a reference output signal, and means for comparing the output signal with the reference output signal and producing a resultant signal which serves as the input signal to the indicator means.

Preferably, the sensor is contained within a casing and is portable. Conveniently, the casing, and thus the sensor as a whole, is sufficiently small to be supported on, and usable in, one hand.

In a preferred embodiment the sensing or sensitive surface of the surface plasmon resonance-sensitive device is enclosed by an enclosure having an inlet means, via which fluid can enter the enclosure and contact the sensing surface, and an outlet means via which the fluid can leave the enclosure. The sensor including the enclosure and its inlet and outlet may be contained within the casing mentioned above. Preferably, means is provided for forcibly causing the fluid to enter the inlet, pass through the enclosure and exit from the outlet. Conveniently, such means may be a fan or blower or pump located in the inlet or outlet.

In one embodiment, the light source, surface plasmon resonance-sensitive device, control means and light detecting means remain in permanently fixed predetermined positions, i.e. they are stationary or static with respect to each other, while the sensor is being used. Thus the control means and light detecting means are at set constant respective angles relative to the surface plasmon resonance-sensitive device. Scanning of neither the incident light nor the reflected light is conducted. The absence of the need to scan and thus the absence of scanning means also facilitates the construction of a small unit.

However, alternatively, the light source and/or surface plasmon resonance-sensitive device and/or control means and/or light detecting means may be movable to or positionable in preset or predetermined positions preparatory to the sensor being used.

The surface plasmon resonance-sensitive device may comprise a propagating medium having a reflecting surface which supports or is coupled to a metallic coating or layer which in turn is covered by or coated with a film of material which is sensitive to the analyte, that is the material is capable of adsorbing or absorbing the analyte. For example, the propagating medium may comprise a glass prism having an internal face constituting the reflecting surface.

The reflecting surface may support the metallic coating directly. Alternatively, the reflecting surface may be coupled to a transparent base member. In the latter arrangement the transparent base member may be a glass slide, such as a glass microscope slide, which is coupled to a glass prism by means of a fluid having a refractive index substantially matching the refractive indices of the glass of the microscope slide and the glass of the prism. Where, for example, a glass prism and glass slide are used the fluid may be glycerol.

In an alternative embodiment of sensor, the reflecting surface may have the form of a grating of suitable pitch with the metallic film being supported or formed directly on the grating.

The sensing material may be an organic material, for example, polypyrrole. Polypyrrole has been found by the present Applicants to be particularly suitable when the sensor is for detecting the presence of MEG in natural gas.

BRIEF DESCRIPTION OF THE DRAWINGS

In order that the invention may be more readily understood, reference will now be made by way of example only, to the accompanying drawings, in which:

FIGS. 4a and 4b are graphs each illustrating the intensity and position of light reflected from the SPR-sensitive device in the presence and absence of analyte.

DETAILED DESCRIPTION OF THE PREFERRED EMBODIMENT

Figure 1:
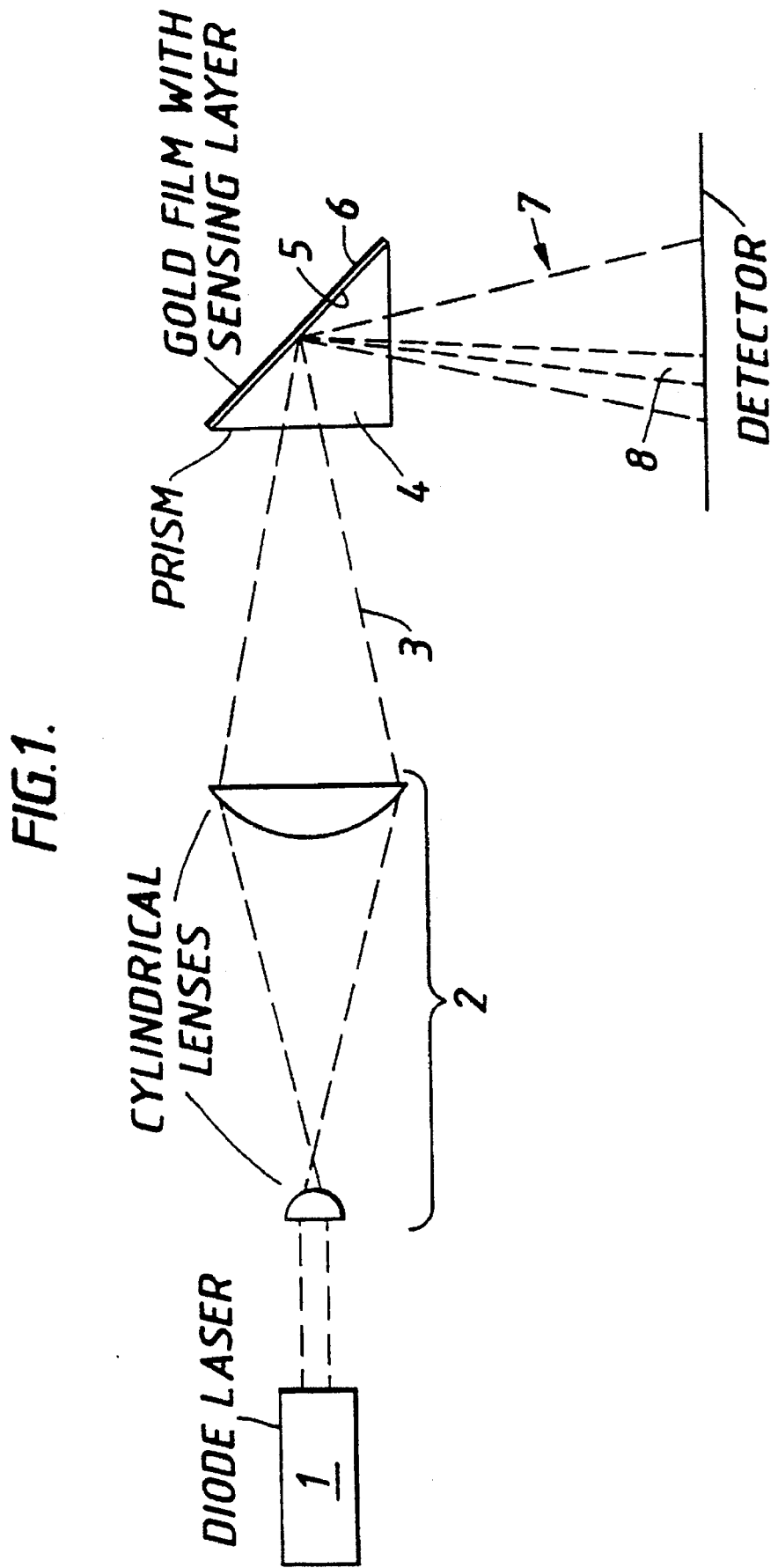
FIG. 1 illustrates schematically and in an idealised manner the kind of effect surface plasmon resonance produces in an optical sensor on which the sensor according to the invention is generally based.

With reference to FIG. 1, a diode laser 1 produces a beam of collimated light which passes through an optical lenses system 2 to produce a converging beam 3 which passes into a prism 4 and is incident at the internal face of reflecting surface 5. The outside of the prism at the reflecting surface is coated with a thin metal film 6, such as a gold film. Light is reflected in the form of a diverging beam 7. For light incident at the internal face of the prism at a specific angle of incidence (contained within the incident angle range of the converging beam) surface plasmon resonance is observed as a dip or reduction in the intensity of reflected light (when compared with reflected light unaffected by the S.P.R. effect) as a result of absorption of light incident at that specific angle due to the presence of the metal film. The region of the reflected beam over which SPR is observed is indicated in FIG. 1 at 8.

Figure 2:
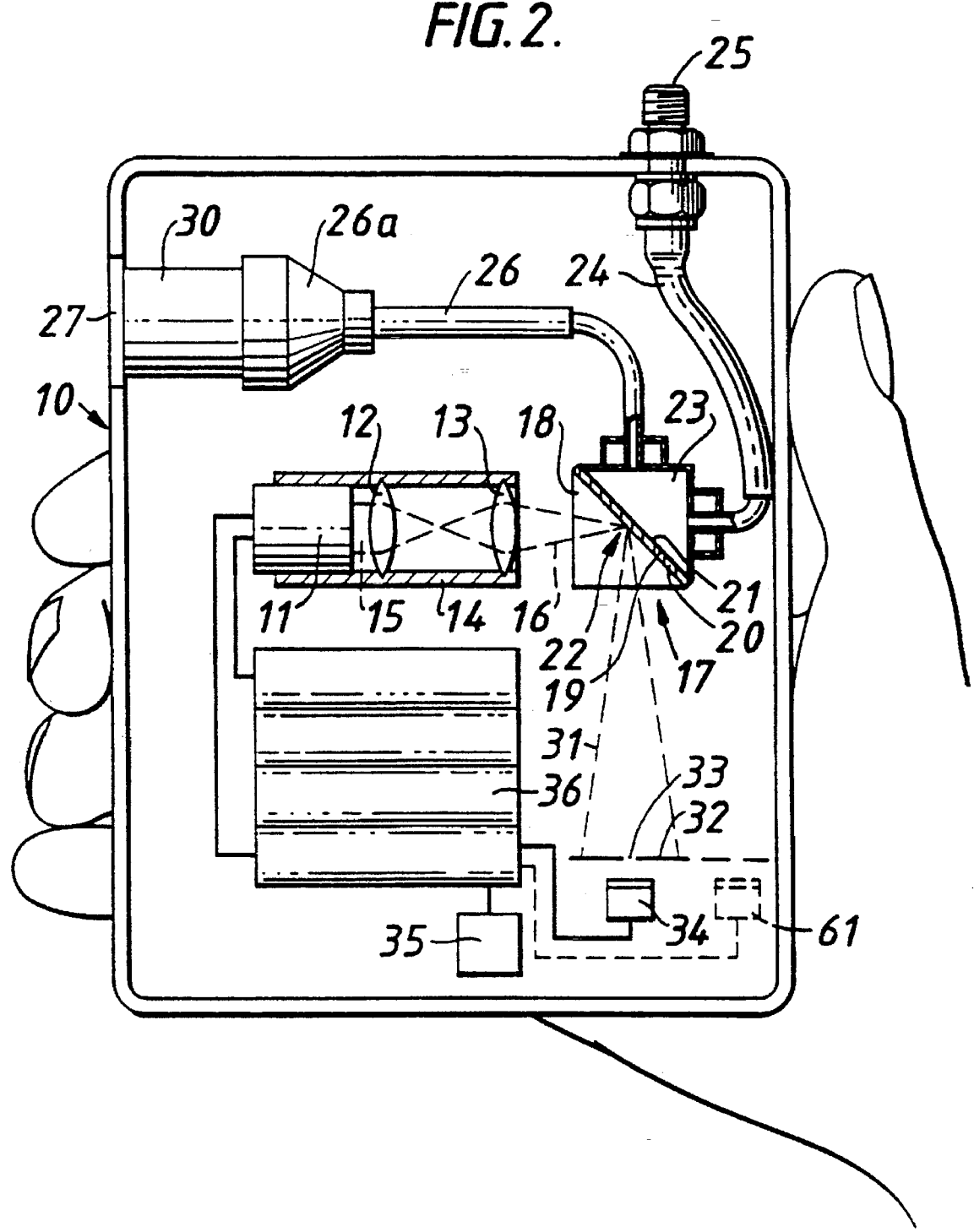
FIG. 2 shows in somewhat schematic form one embodiment of sensor according to the invention.

In FIG. 2 the optical sensor 10 comprises a visible or infrared diode laser module 11 and cylindrical lenses 12 and 13, all of which are rigidly mounted in a holder 14. The diode laser produces a collimated 15 light beam which is formed in to a converging beam 16 and focused to provide incident light on a SPR-sensitive device 17. The wave length of the light may, typically, be about 632 nm. The device 17 comprises a glass prism 18 having a side 19 which provides an internal reflecting surface. In the applicants experiments the prism was made of BK7 glass. The external face of the side 19 is coated with a thin film, coat or layer 20 of a suitable metal, such as gold having a thickness of, typically 40 nm. The gold, in turn, is coated or covered with a thin film 21 of polypyrrole having a thickness of, typically, 100 nm. Together, the gold and polypyrrole provide a region 22 which is sensitive to the presence of MEG. The side of the prism bearing the metal layer 20 and polypyrrole film 21 forms one side of an enclosure constituting a 'gas cell' 23 to which is connected an inlet pipe 24 with an opening 25 via which gas or vapour can enter the gas cell and (influence or) contact the polypyrrole film 21. The gas cell 23 also has connected to it an outlet pipe 26 with an opening 27 via which the gas or vapour can leave the cell.

A pump 30 is located in an enlarged end portion 26a of the outlet pipe 26 in order forcibly or positively to cause gas or vapour being sampled to pass into, through and out of the gas cell 23.

The reflecting region 22 of the SPR-sensitive device 17 causes the converging incident light beam 16 to be reflected as a diverging beam 31 in a manner similar to that indicated schematically in FIG. 1.

A 'pinhole' aperture 33 in an otherwise opaque plate 32 determines the portion of the reflected diverging beam 31 which passes through the plate to be sampled and impinge (or be incident) on one single photodiode 34. The 'pinhole' aperture may, typically, be about 100 to 200 microns in diameter. The portion of the reflected diverging beam which is chosen to be sampled will be indicated below in the descriptions of FIGS. 4A and 4B.

Figure 3:
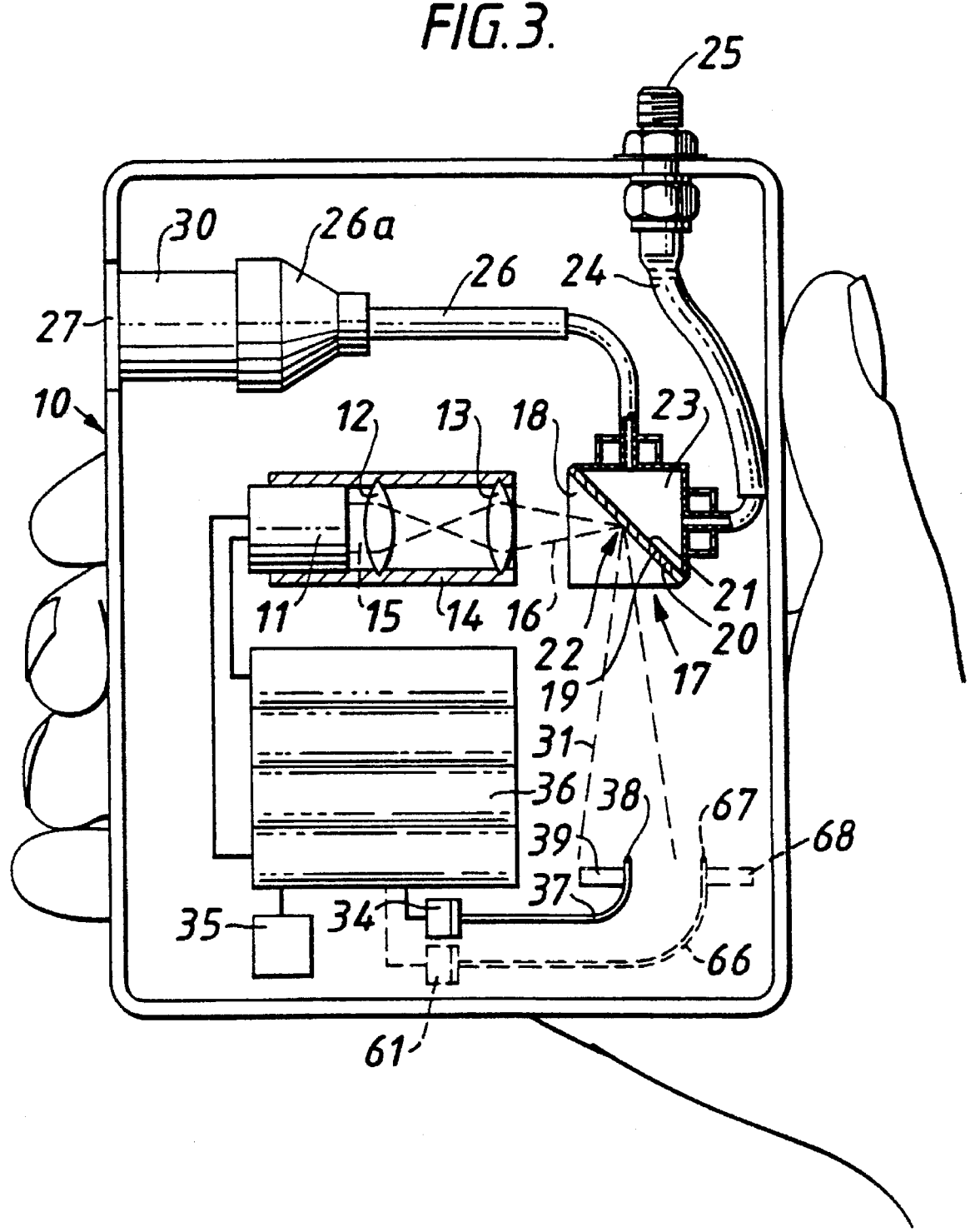
FIG. 3 shows another embodiment of sensor according to the invention.

In FIG. 3, parts of this sensor which are equivalent to parts which have already been described above with reference to FIG. 2 have been identified by the same reference numbers and will not be described any further. In this embodiment an optical fibre 37 replaces the plate 32. The bore (not shown) of the fibre opens at 38 at one end thereof and the fibre is located by a holding means 39 such that the opening 38 is in the same position as the pinhole 33 in the FIG. 2 embodiment. Thus the opening 38 controls or determines the portion of the reflected diverging beam 31 which will be sampled and impinge on the one single photodiode 34 to which the other end of the optical fibre 37 is connected in any suitable manner such that only light emerging from the bore at the said other end of the fibre impinges on the photodiode. The diameter of the bore of the optical fibre 37 is comparable to the diameter of the 'pinhole' aperture in the previous embodiment, that is typically about 100 to 200 microns.

The single photodiode 34 is connected to an indicating means 35 for indicating the presence of the analyte via electrical circuitry 36 which will be described below with reference to FIGS. 5 and 6. The circuitry is mounted on a printed circuit board, and the component parts of the sensor, including the circuit board, are housed in a small casing which can be held in one hand by a user. The casing also houses a compartment for a battery (not shown) for supplying electrical power to operate the sensor. In an alternative embodiment (not shown), the battery compartment in the casing is omitted and a separate battery unit which is electrically connectible to the circuitry in the casing is provided instead.

In the embodiment of sensor shown in FIG. 2, the laser diode 11, prism 18, aperturedplate 32 and photodiode 34 are in permanently but adjustable fixed positions relative to each. Thus, the same portion of the reflected diverging beam will consistently be monitored by the photodiode. The fixed relative positions of these components will have been determined as a result of previously conducted experiments in which different portions of the reflected beam, would have been observed with the components in different relative positions in order to determine the optimum positions. In the FIG. 3 embodiment, the end of the optical fibre having the opening 38 is held in a single fixed predetermined position.

The basis on which the portion of the reflected beam to be monitored is chosen will now be illustrated with reference to FIGS. 4A and 4B.

When analyte is present and influences the sensitive film covering the metal film, the intensity of the reflected light at a fixed position in the reflected beam at which SPR is observed differs from the intensity when the analyte is absent. The effect of SPR observed (in the absence of analyte in the SPR sensitive layer over the metal film) may be represented by the curve 40. On exposure of the SPR sensitive layer to the analyte the effect may be represented by curve 41 in FIG. 4A and by a different curve 42 in FIG. 4B. In FIG. 4A the different positions of the curves 40 and 42k indicate that the range of angles of incidence over which resonance occurs has shifted but with relatively little change in the size and shape of the curve and thus very little change in the intensity of the reflected light in respect of corresponding points on the two curves. The 'pinhole' aperture 33 and photo-detector 34 identified in FIG. 2 are shown in FIGS. 4A and 4B (for illustrative purposes) to indicate the fixed field of view (shown at 43) to which the photodetector is exposed. This field of view is determined, at least in part, by the size, shape and position of the 'pinhole' aperture 33. The photodetector detects changes in reflected light intensity in the field of view within the range 44 resulting from the shifts caused by different concentrations of the analyte in the gas or vapour.

In FIG. 4B the different positions of the curves 40 and 42 indicate that the range of angles of incidence over which resonance occurs has become broader with a lower peak absorption but with relatively little shift having regard to the positions of the two peaks of the curves corresponding to the minimum intensities of reflected light. In these circumstances the photodetector 34 detects change in light intensity in the field of view (shown at 45) within the range 46 resulting essentially from the changes in position of the minimum reflected light intensities within the field of view caused by different concentrations of the analyte in the gas or vapour.

The changes in the curves 41 and 42 shown in the graphs in FIGS. 4A and 4B are illustrative of two extreme idealised situations. In practice an equivalent graph would show the relative position and shape of the curve to be intermediate to the corresponding curves 41 and 42 in FIGS. 4A and 4B.

Figure 5:
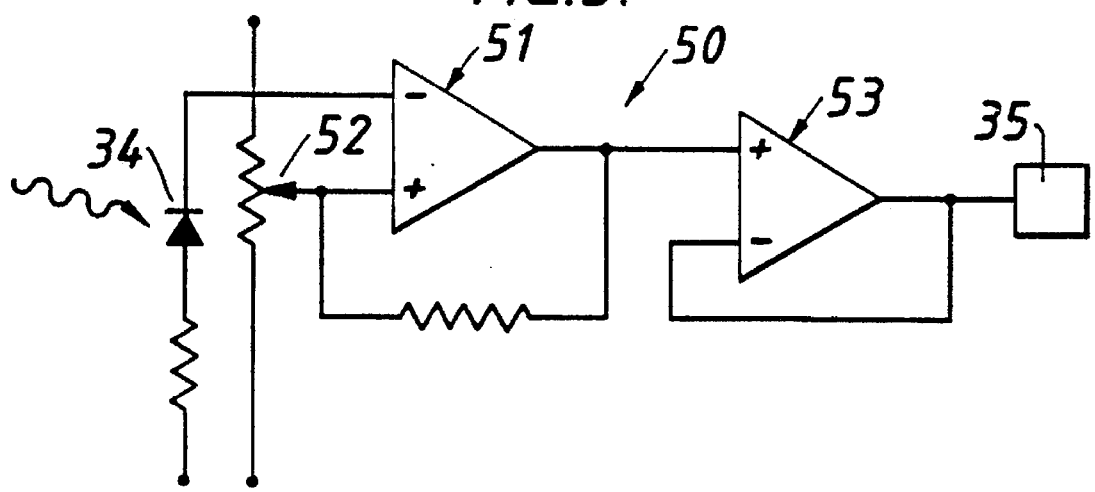
FIG. 5 shows a circuit diagram incorporating the photodetecting means in the sensor in FIG. 2 or FIG. 3.

With reference to the electrical circuit 50 (which forms part of the circuitry 36) in FIG. 5 the output signal from the photodiode 34 is fed to a Schmitt trigger 51.

The switching threshold is set by a potentiometer 52. The output from the trigger 51 is buffered by a voltage follower 53 which produces an output which is fed to the indicating means 35, comprising, for example, a piezoelectric sounder and/or a light emitting diode.

Based on experiments correlating the output from the photodiode with the concentration of MEG in natural gas, the circuit is set such that the indicating means is activated when the concentration of MEG sensed exceeds a preset value.

Figure 6:
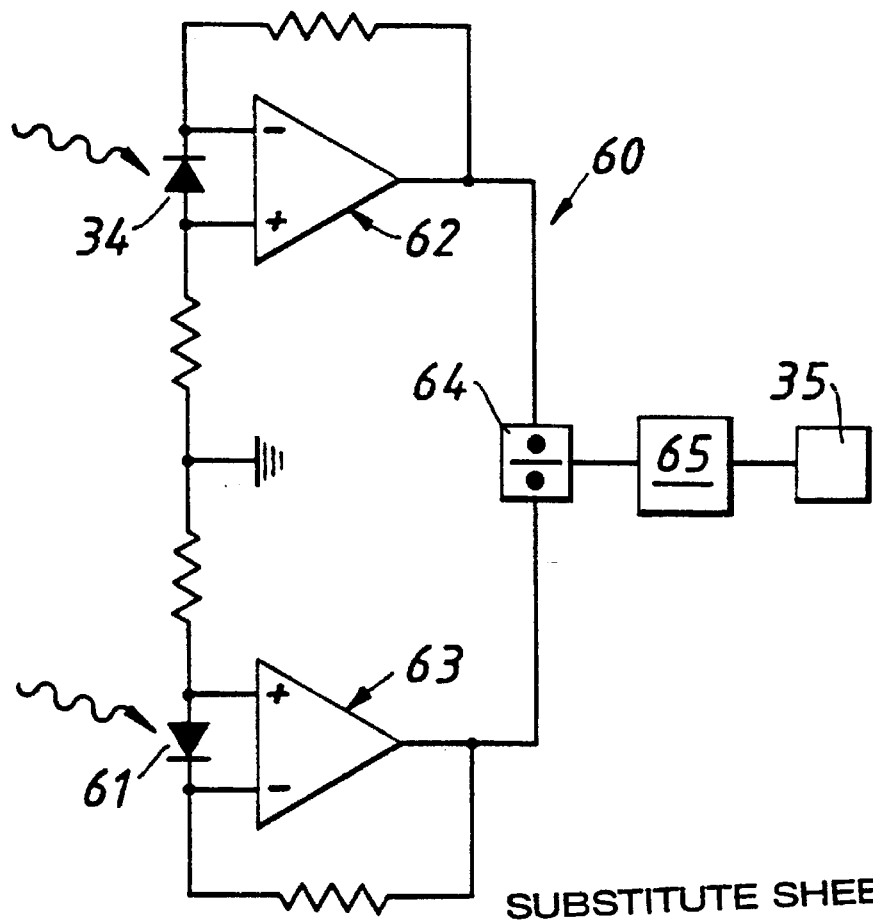
FIG. 6 shows a different circuit diagram incorporating another form of photodetecting means.

With reference to the circuit 60 in FIG. 6, a reference photodiode 61 is provided in addition to the photodiode 34. The reference photodiode is positioned to receive a portion of the reflected beam which is substantially unaffected by the SPR, for example at the positions shown in outline in FIGS. 2 and 3, to provide a constant reference output signal. In FIG. 3, the reference photodiode 61 receives light via an optical fibre 66 having an end which is held in position by a holding means 68 to locate the opening 67 of the bore (not shown) through the optical fibre in the 'reference' position. The output signals from photodiodes 34 and 61 pass to respective amplifiers 62 and 63 from which respective outputs pass to a means for comparing the signals comprising a divider 64 which ratios the two sets of signals. The output from the divider 64 passes to a calibration and driver circuit 65 which produces an output which forms the input to the indicating means 35. The indicating means 35 may be a digital display device or an analogue display device such as a light emitting diode bar graph array which is calibrated in terms of the concentration of MEG in natural gas, utilising correlation between the output from the photodiode with the concentration of MEG, as before.

The use of a diode laser, together with the converging incident beam technique and one single photodiode, as described in connection with the embodiment of sensor in FIG. 2, confer the considerable advantage of enabling the production of a compact, lightweight, low power consuming system. Moreover the construction of the sensor is such that angle scanning is avoided.

The gold film was deposited directly on the external surface of the prism (or on the planar glass slide) by known vacuum evaporation technique.

The polypyrrole was laid down on the metal film by the following electrochemical technique. A conventional electrochemical potentiostat was set up with the gold coated surface of the prism acting as the cathode onto which the film of polypyrrole was to be deposited. A gold coated glass slide was used as the counter electrode and a calomel electrode was used as the reference electrode. A solution containing 0.1 molar concentration of pyrrole and 0.1 molar concentration of potassium chloride with a phosphate buffer was used as the electrolyte. The cell could be operated in either a constant potential mode or a cyclic voltammetry mode. Both techniques were found to produce satisfactory and useable films. The deposition potential was kept below 0.7 volts. Typical deposition times ranged from a few minutes to 10 minutes.

Figure 7:
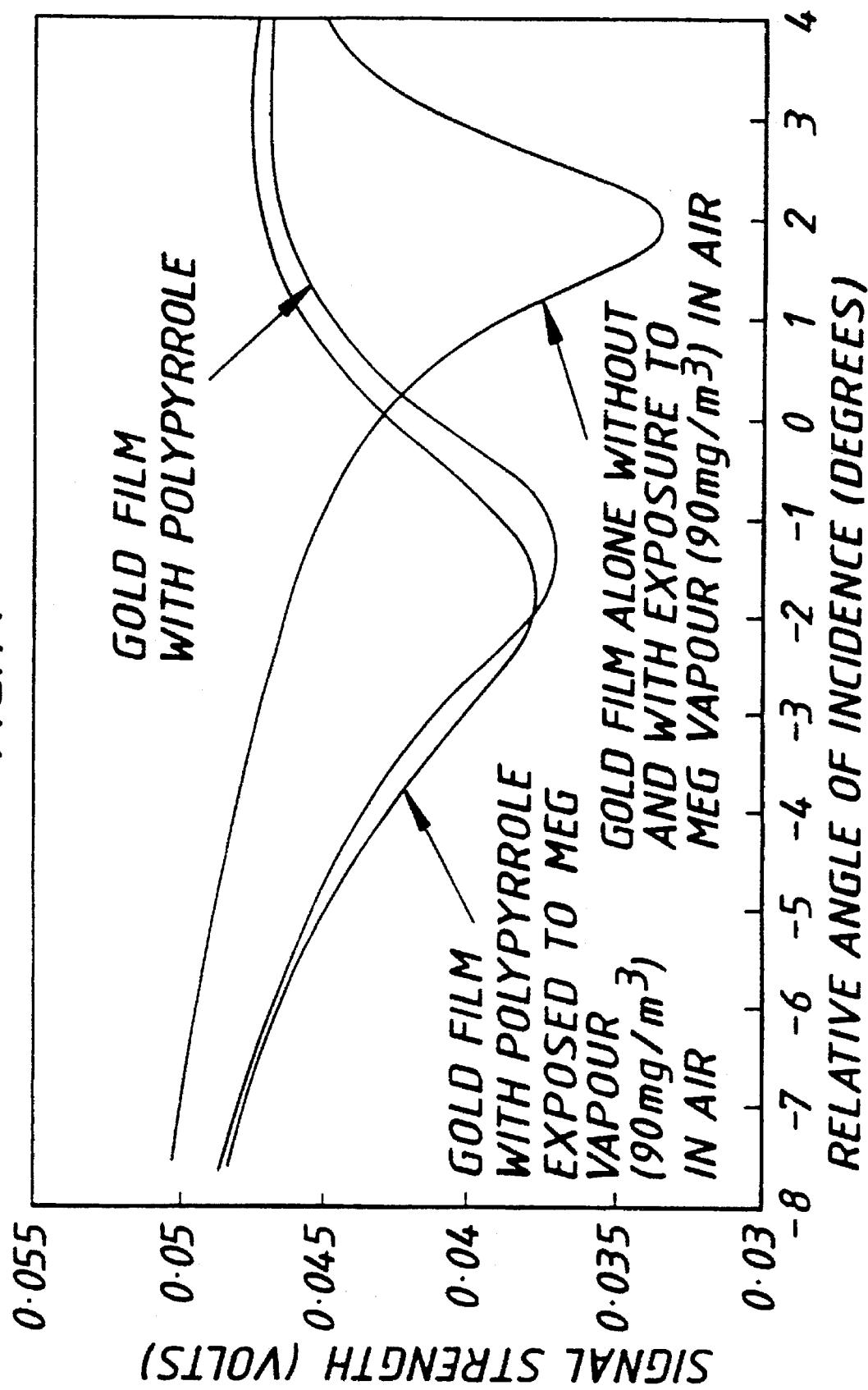
FIG. 7 is a graph illustrating by way of example the effect of the presence of a polypyrrole film on the light reflected from the surface plasmon resonance-sensitive device in the absence and presence of MEG.

When exposed to monoethylene glycol such polypyrrole films give strong reversible SPR shifts which enable the films to be used as a sensing medium for monoethylene glycol. FIG. 7 shows typical results for a polypyrrole film produced after five minutes deposition time.

Although in the above Example the fluid used was a gas or vapour, it will be appreciated that the apparatus could be modified by a man skilled in the art so as to be usable with a liquid which contains the analyte. Thus, the 'gas cell' 23 may be modified, if necessary, so as to be a liquid cell.

We claim:

1. An optical sensor assembly for sensing the presence of analyte in a fluid, comprising:

a surface plasmon resonance-sensitive structure for reflecting light, said structure responding to exposure to an analyte so as to alter an intensity of the reflecting light;

means for producing light focussed on said surface plasmon resonance sensitive structure;

a light detecting means positioned to receive a portion of the light reflected from the surface plasmon resonance-sensitive structure and for producing an output signal in response to the received portion of the reflected light indicative of the presence of, or representative of the concentration or a concentration range of, the analyte in the fluid;

control means for controlling the portion of the reflected light which reaches the light detecting means; and indicating means for receiving the output signal and in response thereto indicating the presence, concentration or concentration range of the analyte in the fluid.

2. A sensor assembly as claimed in claim 1, in which the control means comprises one or more members defining an opening.

3. A sensor assembly as claimed in claim 2, in which the opening is an aperture defined by one member.

4. A sensor assembly as claimed in claim 2, in which the opening is in the form of a slit defined by the one or more members.

5. A sensor assembly as claimed in claim 2, in which the control means comprises an optical fibre with the bore therethrough constituting the opening.

6. A sensor assembly as claimed in claim 1, in which the light detecting means is a photodetecting means.

7. A sensor assembly as claimed in claim 6, in which the photodetecting means comprises one single photodetector.

8. A sensor assembly as claimed in claim 1, in which the light source is a diode laser.

9. A sensor assembly as claimed in claim 1, in which the indicating means indicates the presence of the analyte only when the output signal is representative of a concentration of the analyte that is above a predetermined minimum or threshold value.

10. A sensor assembly as claimed in claim 1, in which the indicating means comprises two or more discrete indicators, each one being representative of a different minimum concentration or range of concentrations of the analyte in the fluid.

11. A sensor assembly as claimed in claim 10, in which the indicators are activated in succession as the signal from the light detecting means increases in magnitude in response to increase in the concentration of the analyte in the fluid.

12. A sensor assembly as claimed in claim 1, in which the indicating means comprises one or more visual indicators.

13. A sensor as claimed in claim 12, in which the or each visual indicator is a light emitting diode.

14. A sensor assembly as claimed in claim 1, contained within a casing and which is small enough and light enough to be portable.

15. A sensor assembly as claimed in claim 14, in which the casing can be supported on one hand.

16. A sensor assembly as claimed in claim 1, in which the sensing surface of the surface plasmon resonance-sensitive structure is enclosed by an enclosure having an inlet means, via which fluid can enter the enclosure and contact the sensing surface, and an outlet means via which the fluid can leave the enclosure.

17. A sensor assembly as claimed in claim 16, comprising means for forceably causing the fluid to enter the inlet, pass through the enclosure and exit from the outlet.

18. A sensor assembly as claimed in claim 17, in which the means is a fan or blower located in the inlet or outlet.

19. A sensor assembly as claimed in claim 1, in which the light source, surface plasmon resonance-sensitive structure, control means and light detecting means are all fixed in position.

20. A sensor assembly as claimed in claim 1, in which one or more of the light source, surface plasmon resonance-sensitive structure, control means and light detecting means are movable to or positionable in preset or predetermined positions with any remaining components or component being fixed in position.

21. A sensor assembly as claimed in claim 1, in which the surface plasma resonance-sensitive structure comprises a propagating medium having a reflecting surface which supports or is coupled to a metallic layer which in turn is covered by a film of material which is sensitive to the analyte.

22. A sensor assembly as claimed in claim 1, wherein the surface plasmon resonance-sensitive structure comprises a propagating medium having a reflecting surface which supports or is coupled to a metallic layer and the metallic layer is covered by a film of material which is sensitive to the analyte, and in which the reflecting surface supports the metallic layer directly.

23. A sensor assembly as claimed in claim 1, wherein the surface plasma resonance-sensitive structure comprises a propagating medium having a reflecting surface which supports or is coupled to a metallic layer and the metallic layer is covered by a film of material which is sensitive to the analyte and in which the reflecting surface is coupled to a base member which directly supports the metallic layer.

24. A sensor assembly as claimed in claim 1, comprising a reflecting surface which has the form of a grating of suitable pitch with a metallic film being supported or formed directly on the grating.

25. A sensor assembly as claimed in claim 1, wherein the surface plasmon resonance-sensitive structure comprises a propagating medium having a reflecting surface which supports or is coupled to a metallic layer and the metallic layer is covered by a film of material which is sensitive to the analyte, and in which the film of material which is sensitive to the analyte is an organic material.

26. A sensor assembly as claimed in claim 25, in which the organic material is polypyrrole.

27. A sensor assembly as claimed in claim 1, comprising a second light detecting means for receiving from the surface plasmon resonance-sensitive structure, reflected light which is unaffected by the presence of the analyte and for producing in response to the reflected light received a reference output signal, and means for comparing the output signal with the reference output signal and producing a resultant signal which serves as the input signal to the indicator means.

28. An optical sensor assembly according to claim 1, wherein said control means comprises members defining an opening which is sufficiently small to permit the passage therethrough of only a very small portion of all the light produced by the light source which has been reflected by the surface plasmon resonance-sensitive structure.

29. An optical sensor according to claim 28, wherein said members defining said opening are positioned so that said opening is positioned relative to said surface plasmon resonance-sensitive structure such that the light produced by the light source which is reflected through said opening by the surface plasmon resonance-sensitive structure is more strongly influenced by the surface plasma and resonance-sensitive structure than light produced by the light source which is reflected by the surface plasmon resonance-sensitive structure but which does not pass through said opening.

30. An optical sensor assembly according to claim 28, wherein the light produced by the light source which is reflected by the surface plasmon resonance-sensitive structure and which passes through said opening is more strongly influenced by the surface plasmon resonance-sensitive structure than light produced by the light source which is reflected by the surface plasmon resonance-sensitive structure but which does not pass through said opening.

31. An optical sensor assembly according to claim 1, wherein said control means comprises a fiber optic sensor which receives only a very small portion of the light produced by the light source which is reflected by the surface plasma and resonance-sensitive structure.

32. An optical sensor according to claim 31, wherein said very small portion is more strongly influenced by the surface plasmon resonance-sensitive structure than the light produced by the light source which is reflected by the surface plasmon resonance-sensitive structure but which is not received by said fiber optic sensor.

33. An optical sensor assembly according to claim 1, wherein said control means comprises a fiber optic detector for detecting light reflected by the surface plasmon resonance-sensitive structure at an angle at which light produced by the light source which is more strongly influenced by the surface plasma and resonance-sensitive structure than at light reflected at other angles from the surface plasmon resonance-sensitive structure.

34. A hand held optical sensor for sensing the presence of analyte in a fluid, comprising:

a light source;

a surface plasmon resonance-sensitive device;

means for focusing light from the light source onto the plasmon resonance-sensitive surface of the device which, in use, reflects the focused light from the light source in the form of a diverging reflected light beam and, on exposure to analyte, responds so as to alter the intensity of the light which is reflected;

a light detecting means for receiving light reflected from the device;

control means for allowing only a portion of that part of the diverging reflected light beam that has been influenced by the surface plasmon resonance effect to reach the light detecting means wherein the light detecting means receives only the influenced portion of the diverging reflected light beam and produces in response to the received portion of the diverging reflected light beam an output signal indicative of the presence of, or representative of the concentration or a concentration range of, the analyte in the fluid; and indicating means for receiving the signal and in response thereto indicating the presence, concentration or concentration range of the analyte in the fluid.

* * * * *